United States Patent [19]

Grohe et al.

[11] Patent Number: 5,077,429

[45] Date of Patent: Dec. 31, 1991

[54] 7-AMINO-1-CYCLOPROPYL-4-OXO-1,4-DIHYDRO-QUINOLINE- AND NAPHTHYRIDINE-3-CARBOXYLIC ACIDS, PROCESSES FOR THEIR PREPARATION AND ANTIBACTERIAL AGENTS CONTAINING THESE COMPOUNDS

[75] Inventors: Klaus Grohe, Odenthal; Hans-Joachim Zeiler, Velbert; Karl G. Metzger, Wuppertal, all of Fed. Rep. of Germany

[73] Assignee: Bayer Aktiengesellschaft, Leverkusen, Fed. Rep. of Germany

[21] Appl. No.: 846,789

[22] Filed: Apr. 1, 1986

Related U.S. Application Data

[60] Division of Ser. No. 807,554, Dec. 11, 1985, Pat. No. 4,620,007, which is a division of Ser. No. 614,923, May 29, 1984, Pat. No. 4,670,444, which is a continuation-in-part of Ser. No. 292,560, Aug. 31, 1981, abandoned, which is a continuation-in-part of Ser. No. 436,112, Oct. 22, 1982, abandoned.

[30] Foreign Application Priority Data

Sep. 3, 1980 [DE] Fed. Rep. of Germany ....... 3033157
Oct. 29, 1981 [DE] Fed. Rep. of Germany ....... 3142854

[51] Int. Cl.$^5$ .............................................. C07C 57/30
[52] U.S. Cl. ...................... 560/51; 544/128; 544/363; 546/156; 546/123; 560/53
[58] Field of Search ................................ 560/51, 53

[56] References Cited

U.S. PATENT DOCUMENTS 3,849,421 11/1974 Nagagome et al. ................. 546/156

FOREIGN PATENT DOCUMENTS

| 0009425 | 4/1980 | European Pat. Off. ............ 544/363 |
| 2343974 | 3/1975 | Fed. Rep. of Germany . |
| 2537047 | 3/1977 | Fed. Rep. of Germany . |
| 2939786 | 4/1980 | Fed. Rep. of Germany ...... 544/363 |

OTHER PUBLICATIONS

Orlita, et al., "Chemical Abstracts", vol. 86, 1977, col. 86:115951d.
Werbel, et al., "Chemical Abstracts", vol. 87, 1977, col. 87:177716k.

*Primary Examiner*—Alan L. Rotman
*Assistant Examiner*—James H. Turnipseed
*Attorney, Agent, or Firm*—Sprung Horn Kramer & Woods

[57] ABSTRACT

The invention relates to 7-amino-1-cyclo-propyl-4-oxo-1,4-dihydro-naphthyridine (or quinoline)-3-carboxylic acids of Formula I as defined in the specification. Also included in the invention is a process for the preparation of said compounds of Formula I and Ia. Further, the invention includes compositions containing the compounds of Formula I or Ia and the use of said compounds and compositions as antibacterial agents.

2 Claims, No Drawings

7-AMINO-1-CYCLOPROPYL-4-OXO-1,4-DIHYDRO-QUINOLINE- AND NAPHTHYRIDINE-3-CARBOXYLIC ACIDS, PROCESSES FOR THEIR PREPARATION AND ANTIBACTERIAL AGENTS CONTAINING THESE COMPOUNDS

This is a division of application Ser. No. 807,554, filed Dec. 11, 1985 now U.S. Pat. No. 4,620,007 which in turn is a divisional of Ser. No. 614,923 filed May 29, 1984 now U.S. Pat. No. 4,670,444 which is a continuation-in-part of our application Ser. No. 292,560 filed Aug. 13, 1981 and a continuation-in-part of our application Ser. No. 436,112 filed Oct. 22, 1982.

The present invention relates to certain new 7-amino-1-cyclopropyl-4-oxo-1,4-dihydro-quinoline- and naphthyridine-3-carboxylic acid compounds, to processes for their production, to their use as antibacterial agents, and to feed additives containing these compounds.

It has already been disclosed that 7-amino-1-ethyl-4-oxo-1,4-dihydro-naphthyridine-3-carboxylic acids have antibacterial properties [see Eur. J. Med. Chem. 12, 541–547 (1977)]; and it has also been disclosed that 1-ethyl-b 6-fluoro-1,4-dihydro-4-oxo-7-piperazino-quinoline-3-carboxylic acids possess antibacterial properties [J. Med. Chem. 23, 1358 (1980)].

According to the present invention there are provided compounds which are 7-amino-1-cyclopropyl-4-oxo-1,4-dihydroquinoline- and naphthyridine-3-carboxylic acids of the formula

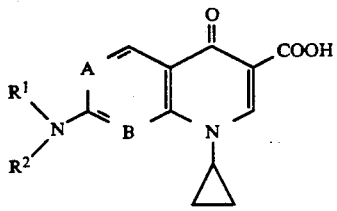

(I)

or a salt thereof, in which

A represents a nitrogen atom or $CR^3$, wherein $R^3$ denotes a hydrogen, a nitro group or a halogen atom (preferably a fluorine or chlorine atom), or a nitrile, carboxamide, carboxyl or ester group, and B represents a nitrogen atom or C—H, and A and B cannot simultaneously be nitrogen atoms, and $R^1$ and $R^2$ are identical or different and represent a hydrogen atom or a straight-chain or branched alkyl, alkenyl or alkinyl radical which has up to 12 (preferably up to 6) carbon atoms and is optionally substituted by radical(s) selected from hydroxyl, alkoxy, alkylmercapto or dialkylamino with 1 to 3 carbon atoms in each alkyl radical, nitrile, alkoxycarbonyl with 1 to 4 carbon atoms in the alcohol part, aryl and hetaryl, or furthermore represent a cycloalkyl radical with 3 to 6 carbon atoms, or, together with the nitrogen atom which they substitute and, if appropriate, a further hetero-atom (such as oxygen or sulphur, or $NR^4$) form a 3-membered to 7-membered ring which can be monosubstituted disubstituted or polysubstituted by radical(s) selected from alkyl or alkenyl with up to 6 carbon atoms, hydroxy, alkoxy or alkyl-mercapto with 1 to 3 carbon atoms, alkoxycarbonyl with 1 to 4 carbon atoms in the alcohol part, nitrile group and aryl, and which can furthermore possess a double bond, and $R^4$ represents a hydrogen atoms, or a branched or straight-chain alkyl, alkenyl or alkinyl group which has up to 6 carbon atoms and is optionally substituted by radical(s) selected from hydroxyl, alkoxy, alkylmercapto or dialkylamino with 1 to 3 carbon atoms per alkyl radical, and alkoxycarbonyl with 1 to 4 carbon atoms in the alcohol part, or represents an aralkyl group which is optionally substituted in the aryl radical by $C_1$–$C_2$-alkyl, halogen, preferably chlorine, $NO_2$ and/or $NH_2$ and has up to 4 (preferably 1 or 2) carbon atoms in the aliphatic part, or an optionally substituted phenyl or naphthyl group or a heterocyclic radical (such as a radical of pyridine, pyrimidine, thiazole or benzothiazole), or $R^4$ denotes an alkoxycarbonyl group which is optionally substituted by an aryl radical and has 1 to 4 carbon atoms in the alcohol part, an alkanoyl radical with 1 to 6 carbon atoms, an aroyl radical, an optionally substituted $C_1$–$C_3$-alkyl- or aryl-(thio) carbamoyl radical, an $C_1$–$C_3$-alkyl- or aryl-sulphonyl radical or an optionally substituted aminosulphonyl radical.

As used herein and unless otherwise specified, the term "aryl" is preferably mono- or bi-cyclic carbocyclic aryl, such as phenyl or naphthyl; the term "aralkyl" is preferably mono- or bi-cyclic carboxylic aryl-$C_1$–$C_4$-alkyl, such as benzyl, phenethyl, naphthyl-methyl and naphthyl-ethyl; the term "hetaryl" is preferably mono- or bi-cyclic, N-, O- or S-heteroaryl, such as pyridine, thiophene and furane; and the term "aroyl" is preferably benzoyl or naphtyoyl.

The compounds of the present invention have a superior antibacterial action against both gram positive and gram negative bacteria, including pseudomonas aerwginosa, to that of the known quinolone- and azaquinolone-carboxylic acids.

The abovementioned aryl radicals, preferably the phenyl or naphthyl radical, are optionally monosubstituted di-substituted or polysubstituted by substituent(s) selected from halogen (preferably fluorine, chlorine and/or bromine), alkyl, alkoxy or alkylmercapto with 1 to 3 carbon atoms, aryloxy or arylmercapto, trifluoromethyl, nitro, nitrile and a carboxylic and ester group with 1 to 4 carbon atoms in the alcohol part.

Further according to the present invention and within the scope of the compounds identified above under Formula (I) there are now provided, as new compounds, 1-cyclopropyl-6-fluoro-1,4-dihydro-4-oxo-7-piperzino-quinoline-3-carboxylic acids of the general formula

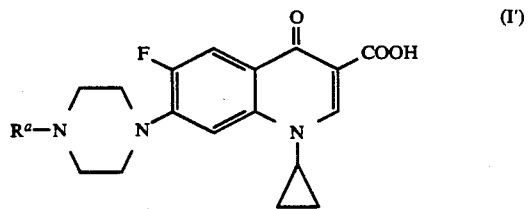

(I')

or salts thereof, in which $R^a$ denotes a hydrogen atom or a methyl, ethyl or β-hydroxyethyl group.

Suitable salts are those of inorganic or organic acids, p.e. hydrochloric acid, hydrobromic acid, hydroiodic acid, sulfuric acid, phosphonic acid, acetic acid, succinic acid, malic acid etc. Suitable salts are furthermore those of anorganic or organic bases, p.e. KOH, NaOH, $Ca(OH)_2$, $Al(OH)_3$, piperidine, morpholine, ethylamine, triethylamine etc. The compounds of the formula (I')
contain various amounts of water.

According to the present invention, there is further provided a process for the production of a compound of the present invention characterized in that a) a quinolone-carboxylic acid of the formula

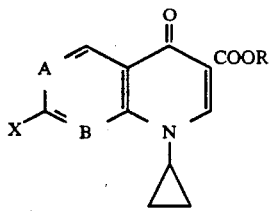

in which
R denotes a hydrogen atom,
A and B have the abovementioned meaning and
X represents a halogen atom or an alkylsulphonyl group with 1 to 4 carbon atoms,
is reacted with an amine of the formula

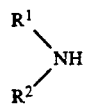

in which $R^1$ and $R^2$ have the abovementioned meanings, or b) a 7-halogeno-naphthyridine-3-carboxylic acid ester of a compound of formula (II), as given above, in which R denotes an alkyl radical and A, B and X have the abovementioned meanings, is reacted with an amine of formula (II), as defined above, if appropriate in the presence of an acid-binding agent, (such as triethylamine or pyridine) and then the resulting 7-amino-naphthyridine-3-carboxylic acid ester is hydrolyzed under alkaline conditions.

If, for example, 7-chloro-1-cyclopropyl-4-oxo-1,4-dihydro-1,6-naphthyridine-3-carboxylic acid and N-methylpiperazine are used as reactants in the reaction, the course of the reaction variant (a) according to the present invention is illustrated by the following equation:

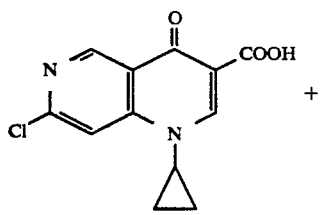

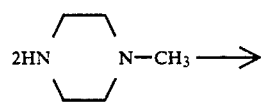

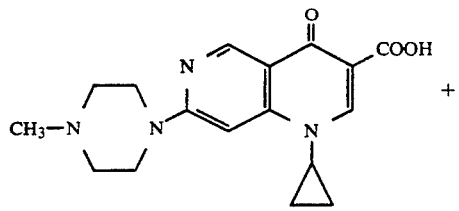

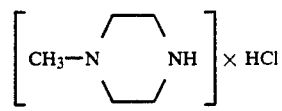

The starting compound of formula (II) can be prepared in the following manner (in which the formulae for the compounds concerned are given in the following reaction scheme):

The starting substance used is, for example, a 4-halogeno-pyridine-3-carboxylic acid ester of the formula (IV), which is substituted by a radical X in the 6-position, this ester is largely converted selectively into a monosubstitution product of the formula (VI), the halogen atom in the 4-position being replaced by the amine radical, with a β-cyclopropylamino-propionic acid ester of the formula (V), preferably a methyl or ethyl ester, which is readily accessible by reaction of corresponding acrylic acid ester with cyclopropylamine. The monosubstitution product of the formula (VI) is converted into a tetrahydro-naphthyridine-3-carboxylic acid ester of the formula (VII) by Dieckmann cyclisation in the presence of a strong base (such as potassium t-butylate or sodium hydride). The carboxylic acid ester of the formula (VIII) is obtained from the ester of formula (VII) with bromine or sulphuryl chloride and triethylamine or pyridine as the dehydrohalogenating agent, and the compound of the formula (VIII) is saponified with an alkali to give the carboxylic acids of the formula (II) (in which R represents a hydrogen atom, A represents a nitrogen atom and B represents CH).

One version of the abovementioned process for the production of a starting substance of formula (II) is represented by the reaction scheme:

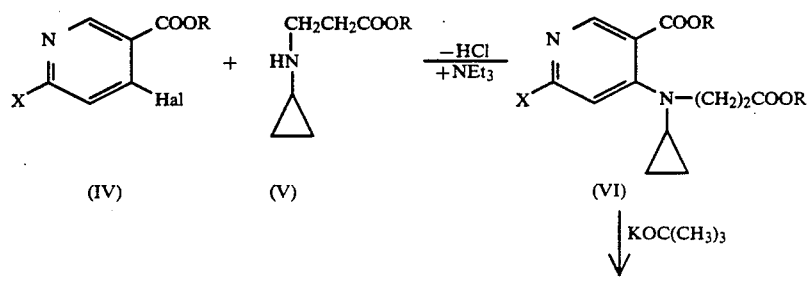

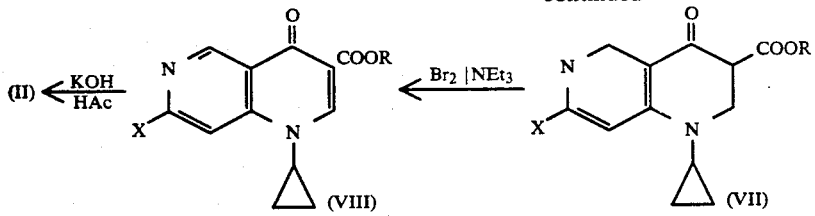

Preferred possible diluents for the reaction variant (a) or (b) are, ethanol, dioxane, toluene, dimethylformamide and dimethylsulphoxide.

Acid-binding agents which can be used in reaction variant (b) are, preferably, alkali carbonates, alkali metal hydroxides or tert.-organic bases (such as, preferably, triethylamine and pyridine).

The reaction temperatures for reaction variants (a) or (b) can be varied within a substantial range. In general, the reaction is carried out at a temperature between 20° C. and 180° C., preferably between 60° and 140°.

Both reaction variants can be carried out under normal pressure, but also under increased pressure, especially in the case of gaseous and low-boiling amines of the formula (III). In general, the reaction is carried out under pressures between 1 and 100 bars, preferably between 1 and 10 bars.

In carrying out reaction variant (a) or (b), 1 to 5 moles of amine, preferably 2 to 3 moles of amine, are employed per mole of carboxylic acid.

The 7-chloro-1-cyclopropyl-4-oxo-1,4-dihydro-1,6-naphthyridine-3-carboxylic acid used as a starting material can be prepared in a multi-stage reaction sequence, for example starting from 4,6-dichloro-nicotinic acid ethyl ester, which is known (see Recueil Trav. chim. Pays-bas. 69, 687 (1950). The methyl ester is known from U.S. Pat. Nos. 4,066,645 and 4,075,210.

According to the present invention there is further provided a process for the production of a compound of the invention of Formula (I') in which (a') 7-chloro-1-cyclopropyl-6-fluoro-1,4-dihydro-4-oxo-quinoline-3-carboxylic acid of the formula

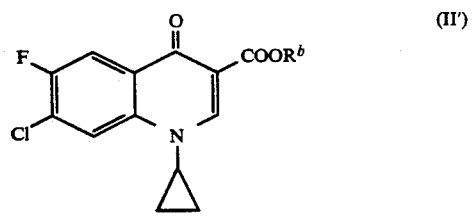

in which $R^b$ denotes a hydrogen atom, is reacted with piperazine or a piperazine derivative of the formula

in which $R^a$ has the meaning given above, or (b') a compound of the formula (II'), as given in reaction variant (a) in which $R^b$ denotes an alkyl group, is reacted with a compound of formula (III') as defined in reaction variant (a), if appropriate, in the presence of an acid-binding agent (such as triethylamine, 1,4-diaza-bicyclo[2,2,2]octane or 1,8-diaza-bicyclo[5,4,0]undec-7-ene) and the 7-piperazino-quinolone-3-carboxylic acid ester obtained is hydrolysed under alkaline conditions to give a compound of formula (I'), and the compound of formula (I') obtained by reaction variant (a) or (b) is converted, if desired, into a salt and/or a hydrate thereof.

The reaction variant (a) is preferably carried out in a diluent (such as dimethylsulphoxide, N,N-dimethylformamide, hexamethyl-phosphoric acid trisamide, sulpholane, water, an alcohol or pyridine) and at a temperature between 20° and 200° C., preferably between 80° and 180° C.

The reaction variants can be carried out under normal pressure, but also under elevated pressure, in particular in the case of a low-boiling solvent. In general, the reaction is carried out under pressures between about 1 and about 100 bar, preferably between 1 and 10 bar.

In carrying out reaction variants 1 to 5 mol of alkylpiperazine (in the case of piperazine 1 to 15 mol), preferably 2 to 3 mol of alkylpiperazine (in the case of piperazine 5 to 10 mol), are employed per mol of carboxylic acid, or carboxylic acid ester of formula (II').

Among the new 1-cyclopropyl-6-fluoro-1,4-dihydro-4-oxo-7-piperazo-quinoline-3-carboxylic acid salts and hydrates of the invention those salts or hydrates that are pharmaceutically acceptable are particularly important and are preferred.

The new free 1-cyclopropyl-6-fluoro-1,4-dihydro-4-oxo-7-piperazino-quinoline-3-carboxylic acids of the general formula (I) and their salts and hydrates can be interconverted in any suitable manner; methods for such interconversion are known in the art.

Thus the 7-piperazino-quinolone-3-carboxylic acids of formula (I) obtained can, if required, be converted into a salt using an organic or inorganic acid. Examples of acids which are suitable for salt formation are hydrohalic acids, such as hydrochloric acid, hydrobromic acid, hydroiodic acid, sulphuric acid, acetic acid, citric acid and benzenesulphonic acid.

If 7-chloro-1-cyclopropyl-6-fluoro-1,4-dihydro-4-oxo-quinoline-3-carboxylic acid and methylpiperazine are used as starting materials in reaction variant (a), the course of the reaction is illustrated by the following equation:

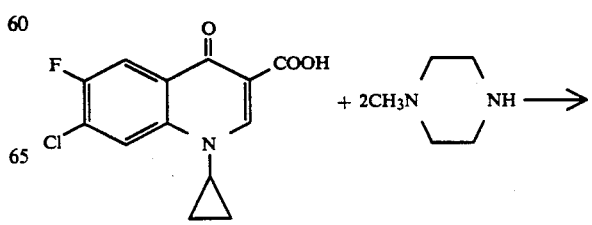

The starting compounds of formula (II') can be prepared via a malonic ester synthesis, according to the following equation:

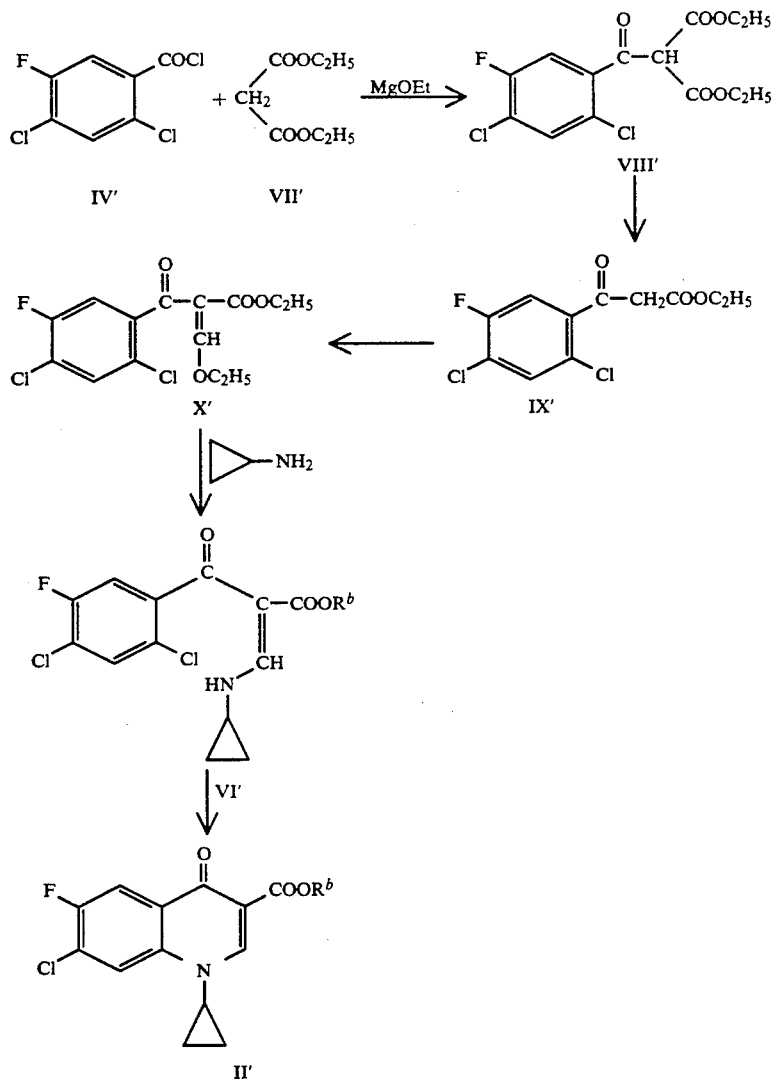

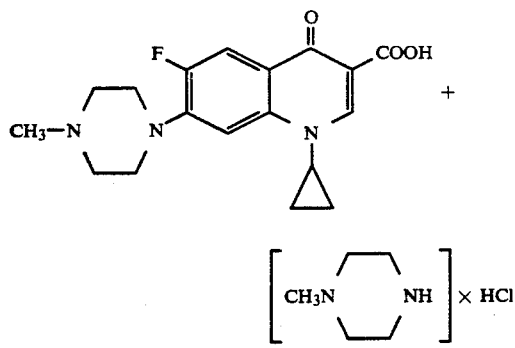

The following may be mentioned individually as active compounds according to the present invention: 7-piperazino-, 7-(4-methylpiperazine)-, 7-(4-ethylpiperazino)-, 7-(4-β-hydroxyethylpiperazino)-1-cyclopropyl-6-fluoro-1,4-dihydro-4-oxo-quinoline-3-carboxylic acid and pharmaceutically tolerated acid addition salts or alkali metal alkaline earth metal or ammonium salts of these compounds.

According to this equation, diethyl malonate of formula (VII) is acylated with a compound of formula (IV') in the presence of magnesium alcoholate to give the acylmalonate of formula (VIII (Organicum, 3rd edition 1964, page 438).

The ethyl aroylacetate of formula (IX') is obtained in good yield by partial hydrolysis and decarboxylation of the compound of formula (VIII') in an aqueous medium containing a catalytic amount of p-toluenesulphonic acid, and is converted with triethyl o-formate/acetic anhydride into the ethyl 2-(2,4-dichloro-5-fluoro-benzoyl)-3-ethoxyacrylate of formula (X'). The reaction of the compound of formula (X') with cyclopropylamine in a solvent (such as methylene chloride, alcohol, chloroform, cyclohexane or toluene) leads to the desired intermediate product of formula (VI) in a slightly exothermic reaction.

The cyclisation reaction VI→II (R$^1$=alkyl) is carried out in a temperature range from 60° to 280° C., preferably 80° to 180° C.

Dioxane, dimethylsulphoxide, N-methyl-pyrrolidone, sulpholane, hexamethylphosphoric acid triamide and preferably N,N-dimethylformamide can be used as diluents.

Potassium t-butanolate, butyl-lithium, lithiumphenyl, phenyl magnesium bromide, sodium ethylate and particularly preferably sodium hydride or potassium carbonate are suitable acid-binding agents for this reaction stage. It can be advantageous to employ an excess of 10 mol % of base.

The 2,4-dichloro-5-fluoro-benzoyl chloride of formula (IV) used as a starting material for this synthesis route, the corresponding carboxylic acid, and the 3-fluoro-4,6-dichlorotoluene of formula (XI) required for the preparation of formula (IV) were not yet known in the literature and form a further subject of the present invention.

The equation below shows the preparation of these precursors or intermediate products, starting from 2,4-dichloro-5-methyl-aniline of formula (XII).

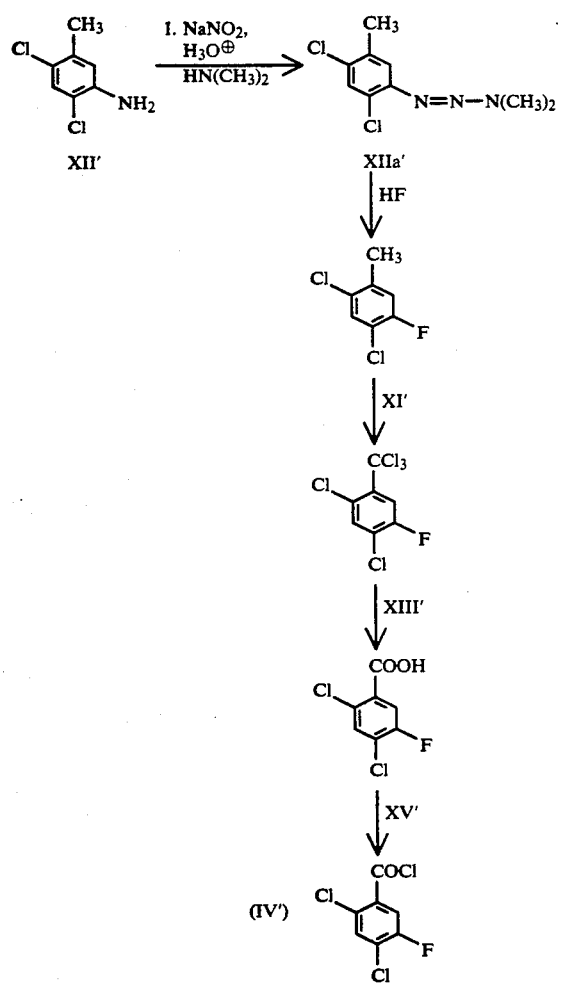

According to this equation, 2,4-dichloro-5-methyl-aniline of formula (XII') is diazotised by means of $NaNO_2$, and the resulting diazonium salt is converted into the triazene of formula (XIIa'), using dimethylamine.

The triazene of formula (XIIa') is dissolved in excess anhydrous HF. In this step, the triazene is cleaved to give 2,4-dichloro-5-methyl-diazonium fluoride and dimethylamine. Without intermediate isolation, this solution is cleaved thermally at 130° to 140° to give 3-fluoro-4,6-dichlorotoluene XI', $N_2$ being split off (Yield: 77.7% of theory).

The 3-fluoro-4,6-dichlorotoluene of formula (XI') is chlorinated in a temperature range from 110° to 160° C., under UV irradiation, to give 2,4-dichloro-5-fluoro-1-trichloro-methylbenzene of formula (XIII').

The hydrolysis of the compound of formula (XIII') with 95 per cent sulphuric acid leads to 2,4-dichloro-5-fluoro-benzoic acid of formula (XV'), which is converted with thionyl chloride into the carboxylic acid-chloride of formula (IV').

The compounds according to the invention are distinguished by a particularly good antibacterial action against gram positive and gram negative bacteria, in particular in comparison with the compounds of German Patent Application P 30 33 157.8 of 3.9.1980 and DE-OS (German Published Specification) 2,804,097, as can be seen from the table below.

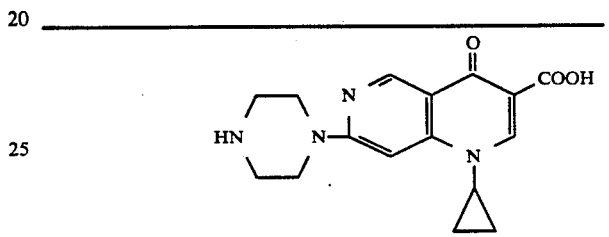

Example 2 of German Patent Application P 30 33 157.8 of 3.9.80

| | |
|---|---|
| Staphylococcus aureus 133 | 8 |
| E. coli A 261 | 1 |
| E. coli Neum. | 1 |
| Klebsiella 8085 | 1 |
| Proteus 1017 | 0.5 |
| Pseudomonas aeruginasa W | 4 |

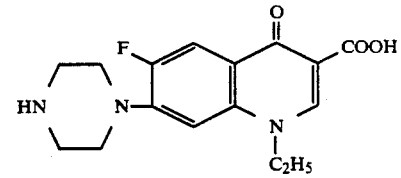

(disclosed in DE-OS (German Published Specification) 2,804,097)

| | |
|---|---|
| Staphylococcus aureus 133 | 1 |
| E. coli A 261 | 0.125 |
| E. coli Neum. | 0.25 |
| Klebsiella 8085 | 0.25 |
| Proteus 1017 | 0.06 |
| Pseudomonas aeruginasa W | 1 |

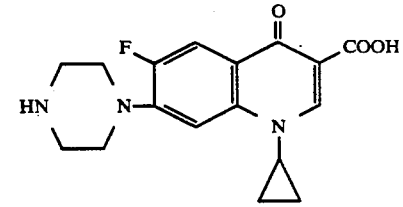

(compound according to the invention, of the formula I (R = H)

| | |
|---|---|
| Staphylococcus aureus 133 | 0.25–0.5 |
| E. coli A 261 | 0.06 |
| E. coli Neum. | 0.06 |

| -continued | |
|---|---|
| Klebsiella 8085 | 0.06 |
| Proteus 1017 | 0.03 |
| Pseudomonas aeruginasa W | 0.5 |

Agar dilution test
DST (dexhase sensitivity test) medium; 1-2 × 10³ germs/plate

New antibacterial active compounds which may be mentioned specifically are: 7-methylamino-, 7-benzylamino-, 7-pyrrolidino-, 7-morpholino-, 7-piperidino-, 7-piperazino-, 7-(4-methylpiperazino)-, 7-(4-benzylpiperazino)-, 7-(4-β-hydroxyethylpiperazino)-, 7-(4-γ-hydroxypropyl-piperazino)-, 7-(4-formylpiperazino)- or 7-(4-hydroxypiperidino)-1-cyclopropyl-4-oxo-1,4-dihydro-1,6-naphthyridine-3-carboxylic acid and pharmaceutically acceptable acid addition salts or alkali or alkaline earth metal salts of these compounds.

It has furthermore been found that the compounds according to the invention have outstanding antimicrobial properties.

In particular, they have a broad bacteriostatic and bactericidal action against Gram-positive bacteria, such as Staphylococci and Streptococci, and Gram-negative bacteria, such as Escherichia, Proteus, Providencia, Enterobacter, Klebsiella, Salmonella and Pseudomonas. The list of sensitive bacteria is to be regarded as a list of examples and in no way restrictive.

The improved broad antibacterial activity of the compounds according to the invention enable them to be used as active compounds both in medicine, in which they can be used both for preventing and for the treatment of systemic or local bacterial infections, in particular of the urinary tract. The compounds according to the invention can furthermore also be used as feed additives for promoting growth and for improving feed utilisation in livestock husbandry, in particular in the rearing of animals for fattening. The active compounds are then preferably administered via the feed and/or the drinking water.

The present invention furthermore relates to agents which contain the new compounds according to the invention. These agents include, for example, feed concentrates, for livestock husbandry, which can also contain, as is customary, vitamins and/or mineral salts, in addition to the active compounds, and pharmaceutical formulations.

Among the new 7-amino-1-cyclopropyl-4-oxo-1,4-dihydro-naphthyridine-3-carboxylic acid salts of the invention, those salts that are pharmaceutically acceptable are particularly important and are preferred, alkali metal salts and alkaline earth metal salts being particularly preferred.

The new free 7-amino-1-cyclopropyl-4-oxo-1,4-dihydro-naphthyridine-carboxylic acids of the general formula (I) and (I') and their salts can be interconverted in any suitable manner; methods for such interconversion are known in the art.

As stated above, the invention also relates to the use in medicine of the compounds of the invention.

The present invention provides a pharmaceutical composition containing as active ingredient a compound of the invention in admixture with an inert pharmaceutical carrier, e.g. a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit from comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical composition according to the invention may, for example, take the form of ointments, gels, pastes, creams, sprays (including aerosols), lotions, suspension, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following:

(a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quarternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelops and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters (e.g. $C_{14}$-alcohol with $C_{16}$-fatty acid)) or mixtures of these diluents.

The pharmaceutical compositions which are ointments, pastes, creams and gels can, for example, contain the usual diluents, e.g. animal and vegetable fats, waves, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example ground nut oil), glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5% usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned diseases in warm-blooded animals, which comprises administering to the animals a compound of the invention alone or in admixture with a diluent or in the form of a medicament according to the invention.

The provision of new bactericides for combating bacteria which are resistant to known bactericides as is the case with compounds of the present invention is an enrichment of the state of the art.

The following examples illustrated but do not limit the invention.

EXAMPLE 1

7-(4-Methylpiperazino)-1-cyclopropyl-4-oxo-1,4-dihydro-1,6-naphthyridine-3-carboxylic acid (a compound of formula (I) in which $R^1R^2N$=4-methylpiperazino, A=N and B=CH).

A suspension of 2.64 g of 7-chloro-1-cyclopropyl-4-oxo-1,4-dihydro-1,6-naphthyridine-3-carboxylic acid and 2.5 g of R-methylpiperazine in 30 ml of ethanol or DMSO (=Dimethylsulfoxide) was heated to the boiling point under reflux for 16 or to 135°-140° C. for two hours. The diluent was distilled off in vacuo, the residue was dissolved in 30 ml of 1N NaOH, the solution was filtered and the filtrate was acidified with 10 strength hydrochloric acid. The precipitate was filtered off and washed with water and ethanol. It could be recrystallised from N-dimethylformamide/ethanol. 3.1 g (94% of the theoretical yield) of 7-(4-methylpiperazino)-1-cyclopropyl-4-oxo-1,4-dihydro-1,6-naphthyridine-3-carboxylic acid of melting point 326° C. (hydrochloride) (decomposition) were obtained.

EXAMPLES 2 TO 10

The carboxylic acids of Examples 2 to 19 were obtained by a procedure analogous to that in Example 1. They are summarised in Table 1. The labelling of the radicals $R^1$ and $R^2$ relates to the formula (I) of the description.

TABLE 1

| Example No. | A | B | $R^1$ | $R^2$ | Decomposition Point (°C.) |
|---|---|---|---|---|---|
| 2 | N | CH | H | $-(CH_2)_2N(CH_2)_2-$ | 322 (hydrochloride) |
| 3 | N | CH | | $-(CH_2)_2O(CH_2)_2-$ | 286 |
| 4 | N | CH | | $-(CH_2)_2CH_2(CH_2)_2-$ | 297 |
| 5 | N | CH | | $-CH_2CH_2CH_2CH_2-$ | 330 |
| 6 | N | CH | | $-(CH_2)_2N(CH_2)_2-$<br>$\vert$<br>$CH_2CH_2OH$ | 305 (hydrochloride) |
| 7 | N | CH | | $-(CH_2)_2N(CH_2)_2-$<br>$\backslash$<br>$(CH_2)_3OH$ | 306 (hydrochloride) |
| 8 | N | CH | | $-(CH_2)_2N(CH_2)_2-$<br>$\vert$<br>$CHO$ | 300 |
| 9 | N | CH | | $-CH_2-CH-(CH_2)_3-$<br>$\vert$<br>$OH$ | 302 |

TABLE 1-continued

| Example No. | A | B | R¹ | R² | Decomposition Point (°C.) |
|---|---|---|---|---|---|
| 10 | N | CH | | $-(CH_2)_2CH(CH_2)_2-$<br>                $\|$<br>                OH | 279 |
| 11 | CF | CH | H | $-(CH_2)_2N(CH_2)_2-$ | 256<br>306 (hydrochloride) |
| 12 | CH | N | | $-(CH_2)_2N(CH_2)_2-$<br>                $\|$<br>                $CH_3$ | 279 |
| 13 | CH | N | | $-(CH_2)_2N(CH_2)_2-$<br>                $\|$<br>                H | 277 |
| 14 | CF | CH | | $-(CH_2)_2N(CH_2)_2-$<br>                $\|$<br>                $CH_3$ | 249 |
| 15 | CF | CH | | $-(CH_2)_4-$ | 323 |
| 16 | C—CN | N | H | $-(CH_2)_2N(CH_2)_2-$ | 335 (hydrochloride) |
| 17 | C—CN | N | | $-(CH_2)_2N(CH_2)_2-$<br>                $\|$<br>                $CH_3$ | 295 (hydrochloride) |
| 18 | C—CN | N | | $-(CH_2)_4-$ | 290 |
| 19 | CF | CH | | $-(CH_2)_2N(CH_2)_2-$<br>                $\|$<br>                $C_2H_5$ | 306 (hydroiodide) |

EXAMPLE 20

Preparation of Precursors a) 6-Chloro-4-(N-2-methoxycarbonylethyl-N-cyclopropyl)-amino-pyridine-3-carboxylic acid methyl ester (a compound of formula (VI) in which R=methyl and X=chlorine).

A mixture of 28.6 g of β-cyclopropylamino-propionic acid methyl ester and 21 g of triethylamine was rapidly added dropwise to a solution of 41.2 of 4,6-dichloropyridine-3-carboxylic acid methyl ester in 150 ml of toluene at 10° to 20° C., whilst cooling with ice and stirring. The ice-bath was removed and the mixture was stirred at room temperature for ¼ hour and heated to the boiling point under reflux for 6 hours. The resulting suspension was washed with water and dried with Na₂SO₄ and the solvent was distilled off in vacuo. 59 g of the title compound were obtained as a brown oil.

b) The β-cyclopropylaminopropionic acid methyl ester

This compound, used as a reactant in Example 20 a), was prepared as follows:

86 g of freshly distilled methyl acrylate which had been cooled to −60° C. was added dropwise to a solution, which had been cooled to −60° C. to −70° C., of 57 g of cyclopropylamine in 150 ml of ethanol in the course of about 3 hours. The mixture was then allowed to rise slowly to room temperature overnight, the solvent was distilled off in vacuo and the residue was then fractionated. 95 g of β-cyclopropylamino-propionic acid methyl ester passed over at 84°–86° C./22 mm Hg.

c) 7-Chloro-1-cyclopropyl-4-oxo-1,2,3,4-tetrahydro-1,6-naphthyridine-3-carboxylic acid methyl ester (a compound of formula (VII) in which R=methyl and X=chlorine).

59 g of crude 6-chloro-4-(N-2-methoxycarbonylethyl-N-cyclopropyl)-amino-pyridine-3-carboxylic acid methyl ester were dissolved in 240 ml of anhydrous toluene, and 23 g of potassium t-butylate were rapidly added, whilst stirring. The mixture was left to stand overnight, 20 g of glacial acetic acid and 100 ml of water were added, the phases were separated, the toluene solution was washed again with water and dried with Na₂SO₄ and the toluene was stripped off in vacuo. After recrystallisation from methanol, 18 g of the carboxylic acid ester of melting point 155° to 157° C. were obtained.

d) 7-Chloro-1-cyclopropyl-4-oxo-1,4-dihydro-1,6-naphthyridine-3-carboxylic acid methyl ester (a compound of formula (VIII) in which R=methyl and X=chlorine).

9.8 g of the tetrahydronaphthyridine-3-carboxylic acid methyl ester prepared according to Example 20 c) were dissolved in 200 ml of methylene chloride, and a solution of 5.9 g of bromine in 40 ml of CH₂Cl₂ was rapidly added dropwise at 10° to 15° C. whilst cooling with ice. The mixture is then stirred at ∼10° C. for a further 10 minutes, 8 g of triethylamine were added and the ice-bath was removed. The mixture was subsequently stirred for 3 hours, washed twice with water and dried with Na₂SO₄, the solvent was distilled off in vacuo and the residue was recrystallised from dimethylformamide/ethanol. 8.8 g of 7-chloro-1-cyclopropyl-4-oxo-1,4-dihydro-naphthyridine-3-carboxylic acid methyl ester of melting point 272° to 274° C. (decomposition) were obtained.

e) 7-Chloro-1-cyclopropyl-4-oxo-1,4-dihydro-1,6-naphthyridine-3-carboxylic acid (a compound of formula (II) in which R=H, A=N, B=CH and X=chlorine).

A solution of 5.7 g of potassium hydroxide in 300 ml of water was added to 27.85 g of the ester prepared according to Example 11 d). The mixture was heated to 85° to 95° C. for 30 minutes, whilst stirring, and the resulting solution was filtered at room temperature and acidified with glacial acetic acid. The precipitate was filtered off, washed with water and dried over calcium chloride in a vacuum drying cabinet. 20 g of pure 7-chloro-1-cyclopropyl-4-oxo-1,4-dihydro-1,6-naphthyridine-3-carboxylic acid of melting point 226° to 227° C. were obtained. (including prevention, relief and cure of) the above-mentioned diseases in warm-blooded animals, which comprises administering to the animals a compound of the invention alone or in admixture with a diluent or in the form of a medicament according to the invention.

The present invention further provides a feed additive comprising an active compound of the present invention in admixture with a feed additive-carrier.

The examples which follow illustrate the invention further.

EXAMPLE 21

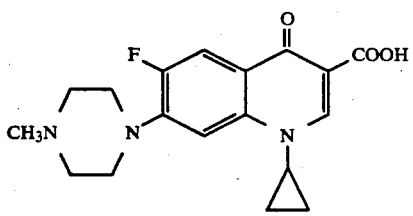

A mixture of 20 g of 7-chloro-1-cyclopropyl-6-fluoro-1,4-dihydro-4-oxo-quinoline-3-carboxylic acid, 28.5 g of N-methylpiperazine and 120 ml of anhydrous dimethylsulphoxide was heated at 135° to 140° C. for 1.5 hours. The solvent was distilled off under a fine vacuum, and the residue was suspended in approx. 50 ml of $H_2O$. The suspension was filtered under suction, and the residue was rinsed with $H_2O$, dried in a vacuum drying cabinet at 80° C. over $CaCl_2$, and recrystallised from glycol monomethyl ether. 14.5 g of 1-cyclopropyl-6-fluoro-1,4-dihydro-7-(4-methylpiperazino)-4-oxo-quinoline-3-carboxylic acid which decomposes at 248° to 250° C. were obtained.

EXAMPLE 22

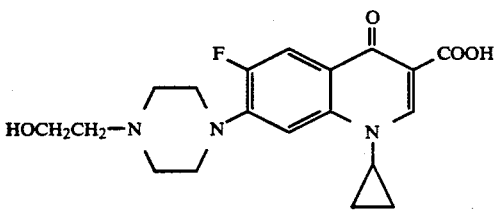

A suspension of 2.81 of 7-chloro-1-cyclopropyl-6-fluoro-1,4-dihydro-4-oxo-quinoline-3-carboxylic acid and 5.2 g of N-β-hydroxyethylpiperazine in 25 ml of dimethylsulphoxide was heated at 135° to 140° C. for 2 hours. The solvent was distilled off under a fine vacuum, the residue was boiled for a short time with 20 ml of $H_2O$ and left to stand overnight at room temperature, and the precipitate was filtered off under suction, while cooling with ice, and was washed with water and dried in vacuo over $CaCl_2$ at 80° C. 2.1 g of 1-cyclopropyl-6-fluoro-1,4-dihydro-4-oxo-7-(4-β-hydroxyethyl-piperazino)-quinoline-3-carboxylic acid which decomposed at 237° to 239° C. were obtained.

EXAMPLE 23

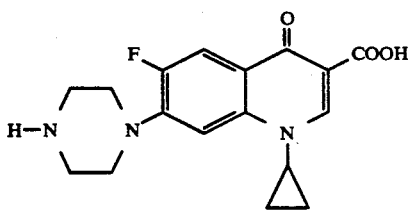

A mixture of 19.7 g of 7-chloro-1-cyclopropyl-6-fluoro-1,4-dihydro-4-oxo-quinoline-3-carboxylic acid, 30.1 g of anhydrous piperazine and 100 ml of dimethylsulphoxide was heated at 135° to 140° C. for 2 hours. The solvent was distilled off under a fine vacuum, and the residue was suspended in $H_2O$, filtered off under suction and washed with water. For further purification, the moist crude product was boiled with 100 ml of water, filtered off under suction at room temperature, washed with $H_2O$ and dried over $CaCl_2$ in a vacuum drying cabinet at 100° C. until its weight remained constant. 19.6 g of 1-cyclopropyl-6-fluoro-1,4-dihydro-4-oxo-7-piperazinoquinoline-3-carboxylic acid which decomposed at 255° to 257° C. were obtained.

The compound prepared according to Example 3 was dissolved in 50 ml of hot 10 per cent hydrochloric acid. 150 ml of ethanol were added to the filtered solution, the mixture was cooled with ice, and the product was filtered off under suction, washed with alcohol, and dried in vacuo at 100° C. 18.5 g of 1-cyclopropyl-6-fluoro-1,4-dihydro-4-oxo-7-piperazino-quinoline-3-carboxylic acid hydrochloride were obtained as colourless crystals which decomposed at 326°-328° c. The monohydrate of this hydrochloride has a m.p. 318°—320° C.

EXAMPLE 24

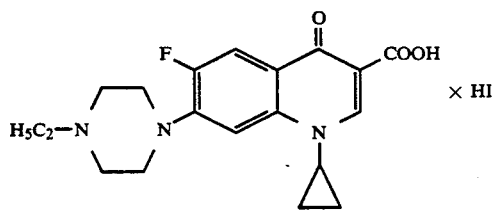

a) A mixture of 1.2 g of 1-cyclopropyl-6-fluoro-1,4-dihydro-4-oxo-7-piperazino-quinoline-3-carboxylic acid, 1.13 g of ethyl iodide, 0.73 g of triethylamine and 20 ml of N,N-dimethylformamide was heated at 70° to 80° C. for 2.5 hours. The solvent was distilled off in vacuo, and the residue was suspended in water. The product was filtered off under suction, rinsed with $H_2O$ and pressed on clay. 1.15 g of 1-cyclopropyl-6-fluoro-7-(ethylpiperazino)-1,4-dihydro-4-oxo-quinoline-3-carboxylic acid hydroiodide which decomposes at 306° C. were obtained.

b) The 7-chloro-1-cyclopropyl-6-fluoro-1,4-dihydro-4-oxo-quinoline-3-carboxylic acid used as the starting material was prepared as follows:

24.3 g of magnesium turnings were suspended in 50 ml of anhydrous ethanol. 5 ml of carbon tetrachloride were added and, when the reaction had started, a mixture of 160 g of diethyl malonate, 100 ml of absolute ethanol and 400 ml of anhydrous ether was added dropwise, a vigorous reflux being observed. After the reaction had ceased, the mixture was heated at the boil for a further 2 hours and was cooled with dry ice/acetone at 315° C. to −10° C. and a solution of 227.5 g of 2,4-dichloro-5-fluoro-benzoyl chloride in 100 ml of absolute ether was slowly added dropwise at this temperature. The mixture was stirred for 1 hour at 0° C. to −5° C. and was allowed to reach room temperature overnight, and a mixture of 400 ml of ice-water and 25 ml of concentrated sulphuric acid was allowed to run in while cooling with ice. The phases were separated and were extracted twice with ether. The combined ether solutions were washed with saturated NaCl solution and dried with $Na_2SO_4$, and the solvent was stripped off in vacuo. 349.5 g of diethyl 2,4-dichloro-5-fluoro-benzoyl-malonate were obtained as the crude product.

0.15 g of p-toluenesulphonic acid was added to an emulsion of 34.9 g of crude diethyl 2,4-dichloro-5-fluorobenzoyl-malonate in 50 ml of water. The emulsion was heated at the boil for 3 hours while stirring thoroughly, and, when cold, was extracted several times with methylene chloride, the combined $CH_2Cl_2$ solutions were washed once with saturated NaCl solution and dried with $Na_2SO_4$, and the solvent was distilled off in vacuo. Fractionation of the residue under a fine vacuum gave 21.8 g of ethyl 2,4-dichloro-5-fluoro-benzoyl acetate IX of boiling point 127° to 142° C/0.09 mbar.

A mixture of 21.1 g of ethyl 2,4-dichloro-5-fluoro-benzoyl-acetate, 16.65 g of ethyl o-formate and 18.55 g of acetic anhydride was heated at 150° C. for 2 hours. The volatile constituents were then distilled off under a waterjet vacuum and finally under a fine vacuum, at a bath temperature of 120° C. 25.2 g of crude ethyl 1-(2,4-dichloro-5-fluoro-benzoyl)-3-ethoxy-acrylate remained. It was sufficiently pure for the further reactions.

4.3 g of cyclopropylamine were added dropwise to a solution of 24.9 of ethyl 2-(2,4-dichloro-5-fluoroben-zoyl)-3-ethoxy-acrylate in 80 ml of ethanol while cooling with ice and stirring. When the exothermic reaction had ceased, the mixture was stirred for another hour at room temperature, the solvent was stripped off in vacuo, and the residue was recrystallised from cyclohexane/petroleum ether. 22.9 g of ethyl 2-(2,4-dichloro-5-fluoro-benzoyl)-3-cyclopropylamino-acrylate ($R^1=C_2H_5$) of melting point 89° to 90° C were obtained.

3.44 g of 80 per cent sodium hydride were added in portions to a solution of 31.9 g of ethyl 2-(2,4-dichloro-5-fluoro-benzoyl)-3-cyclopropylamino-acrylate ($R^1=C_2H_5$) in 100 ml of anhydrous dioxane while cooling with ice and stirring. The mixture was then stirred at room temperature for 30 minutes and under reflux for 2 hours, and the dioxane was stripped off in vacuo. The residue (40.3 g) was suspended in 150 ml of water, 6.65 g of caustic potash were added, and the mixture was refluxed for 1.5 hours. The warm solution was filtered and the residue was rinsed with $H_2O$. The filtrate was then acidified to pH=1 to 2 with semiconcentrated hydrochloric acid, while cooling with ice, and the precipitate was filtered off under suction, washed with water and dried in vacuo at 100° C. 27.7 g of 7-chloro-1-cyclopropyl-6-fluoro-1,4-dihydro-4-oxo-quinoline-3carboxylic acid ($R^1=H$) of melting point 234° to 237° C. were obtained in this manner.

The present invention also comprises pharmaceutically acceptable bioprecursors of the active compounds of the present invention. The following example shows the recipe of a table according to the invention:

| | | |
|---|---|---|
| 1-Cyclopropyl-6-fluoro-1,4-dihydro-4-oxo-7-piperazino-3-carboxylic acid HCl | 277.5 mg | (corresponding to 250.0 mg Betain) |
| Avicel | 49.0 mg | |
| Moist corn starch | 14.0 mg | |
| Pregelatiniged starch | 6.0 mg | |
| Magnesium stearate | 3.5 mg | |
| tablet without film coating | 350.0 mg | |

| -continued | |
|---|---|
| Film coating | |
| HPM cellulose 15 cp | 3.0 mg |
| Polyethylene glycol 4000 | 1.0 mg |
| Titanium dioxide | 1.0 mg |
| film coated tablet | 355.0 mg |

For the purposes of this specification the term "pharmaceutically acceptable bioprecursor" of an active compound of the invention means a compound having a structural formula different from the active compound but which nonetheless, upon administration to a warm-blooded animal is converted in the patient's body to the active compound.

The improved bacterial action of the compounds of Example 1 according to the present invention is particularly clear in the following biotest Example, in which it was compared with 2-piperazino-8-ethyl-5-oxo-5,8-dihydropyrido 2,3-d pyrimidine-6-carboxylic acid ("pipemidic acid") or the known compound 1-ethyl-7-methyl-1,8-naphthyrid-4-one-3-carboxylic acid ["nalidixic acid"; Ehrhart/Ruschig, Arzneimittel (Medicaments), Volume 2: Chemotherapeutika (Chemotherapeutics), Verlag Chemie 1968, page 1,568]. The compound of the invention have proved to be far superior in vitro and in vivo on bacteria such as Staphylococci, Escherichia coli, Proteus, Klebsiella and Pseudomonas than such known compounds.

EXAMPLE

The agar dilution test was carried out by the Denly multipoint inoculation method and the results were as shown in the following Table.

| | Minimum inhibitory concentrations mog/ml in an agar dilution test[x)] | | |
|---|---|---|---|
| | Compounds from Example 1 | Pipemidic acid | Nalidixic acid |
| *Escherichia coli* | | | |
| T 7 | 0.25 | 2 | 1 |
| 455/7 | 128 | 128 | 256 |
| 103400 | 0.25 | 1 | 2 |
| Salmonella 683 | 0.5 | 2 | 4 |
| Klebsiella 63 | 1 | 2 | 4 |
| Pseudomonas 7167 | 8 | 16 | 64 |
| Proteus 8228 | 2 | 4 | 8 |

[x)]Denley multipoint inoculation method

The present invention also comprises pharmaceutically acceptable bioprecursors of the active compounds of the present invention.

For the purposes of this specification the term 'pharmaceutically acceptable bioprecursor' of an active compound of the invention means a compound having a structural formula different from the active compound but which nonetheless, upon administration to a warm-blooded animal is converted in the patient's body to the active compound.

What is claimed is:
1. Ethyl 2,4-dichloro-5-fluorobenzoyl-acetate.
2. Ethyl 2-(2,4-dichloro-5-fluorobenzoyl)-3-ethoxyacrylate.

* * * * *